(12) United States Patent
Yu

(10) Patent No.: US 6,253,387 B1
(45) Date of Patent: Jul. 3, 2001

(54) GOGGLES HAVING DIFFERENT DEGREES OF STIFFNESS

(76) Inventor: Wen-Hao Yu, 1F, No. 10, Alley 28, Lane 248, Jeng-Jung Rd., Shu-Lin Chen, Taipei Hsien (TW)

(*) Notice: Subject to any disclaimer, the term of this patent is extended or adjusted under 35 U.S.C. 154(b) by 0 days.

(21) Appl. No.: 09/460,627

(22) Filed: Dec. 14, 1999

(51) Int. Cl.[7] .................................................. A61F 9/02
(52) U.S. Cl. .................................................. 2/428; 2/445
(58) Field of Search .............................. 2/426–428, 430, 2/439, 440, 445, 448, 454

(56) References Cited

U.S. PATENT DOCUMENTS

| | | | | |
|---|---|---|---|---|
| 5,495,623 | * | 3/1996 | Leonardi ................................... | 2/431 |
| 5,642,178 | * | 6/1997 | Leonardi et al. ......................... | 351/111 |
| 5,644,800 | * | 7/1997 | Leonardi ................................... | 2/431 |
| 5,650,866 | * | 7/1997 | Haslbeck .................................. | 359/43 |
| 5,862,529 | * | 1/1999 | Moodie et al. ........................... | 2/431 |
| 5,915,542 | * | 6/1999 | Swiet ....................................... | 2/441 |
| 6,119,279 | * | 9/2000 | Haslbeck .................................. | 2/445 |

* cited by examiner

Primary Examiner—John J. Calvert
Assistant Examiner—Katherine Moran
(74) Attorney, Agent, or Firm—Brinks Hofer Gilson & Lione

(57) ABSTRACT

A goggles assembly has a one-piece molded frame which includes a pair of lens rims, a bridge interconnecting the lens rims, and a pair of looped protective pads connected to and lining the lens rims. The lens rims have a stiffness sufficient to resist deformation caused by a pulling force. The bridge has a stiffness different from that of the lens rims. The protective pads have flexibility and softness sufficient to flex so as to conform to the profile of a wearer's face. The molded frame is fabricated from at least two different molding compositions, one of which has high stiffness to impart rigidity to the lens rims, and the other one of which imparts good flexibility to the protective pads.

15 Claims, 5 Drawing Sheets

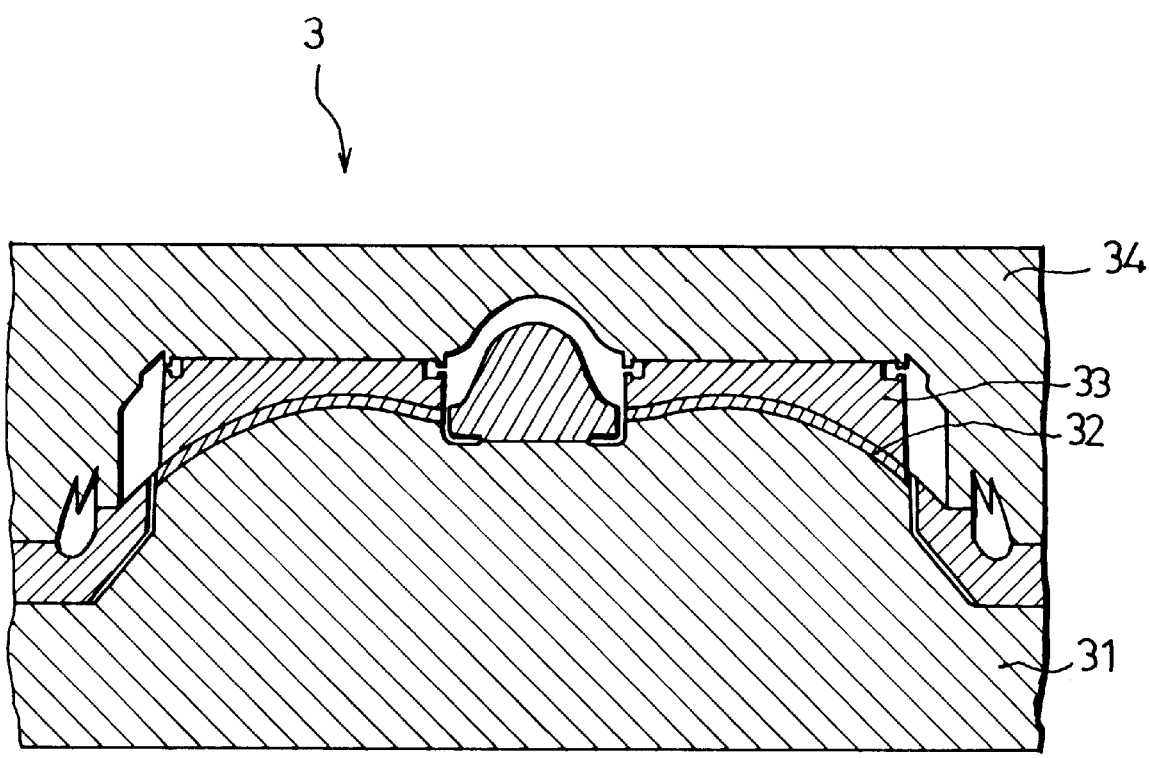
F I G. 4

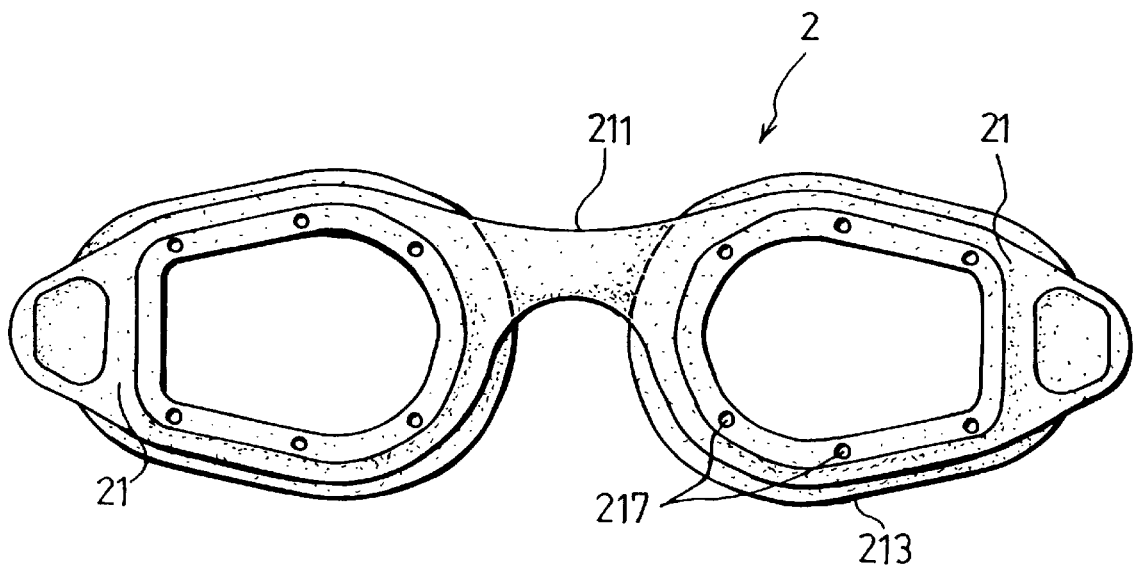
F I G. 5
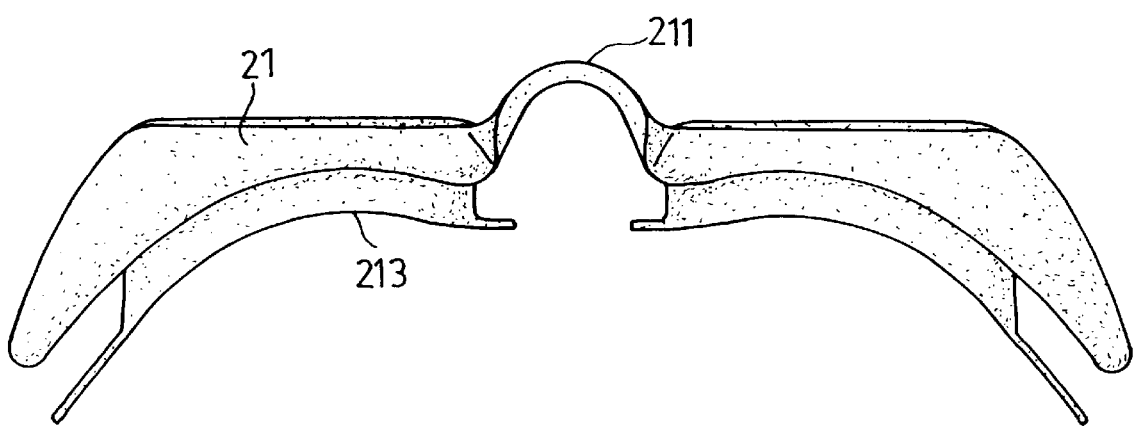
F I G. 6

GOGGLES HAVING DIFFERENT DEGREES OF STIFFNESS

BACKGROUND OF THE INVENTION

1. Field of the Invention

The invention relates to a goggles assembly, more particularly to a goggles assembly having different degrees of stiffness in its component parts, such as lens rims, a bridge interconnecting the lens rims, and protective pads.

2. Brief Description of the Related Prior Art

Owing to the growing popularity of swimming as a form of exercise, there is an increasing demand for personal articles, such as swimming suits, caps, goggles, etc. Swimming goggles have been commonly used by people in order to protect their eyes from intrusion of water and other undesirable matter while swimming in water. Generally, a typical swimming goggles is formed integrally via an injection molding method in which a molding material is placed in an extruding machine and then heated and injected into a mold to form a unitary goggles. As shown in FIGS. 1 and 2, the goggles 1 formed by injection molding includes a goggles frame which includes a pair of rims 11, a bridge 111 interconnecting the rims 11, and protective pads 12 formed along the rims 11. The goggles frame 1 is made from a single material by injection molding, and thus exhibits the same softness or hardness, the same characteristics and the same color in all parts of the rims 11, the bridge 111 and the protective pads 12. However, as the protective pads 12 formed along the rims 11 function to protect the eyes and prevent intrusion of water, they must possess a softness and flexibility necessary to render the former to contact intimately the user's face around the eyes. But, if the goggles frame is made of a material having a good softness for the protective pads 12, the rims will accordingly have an increased softness so that, when the user wears the goggles, the goggles will be pulled and stretched and the soft rims would deform, thereby resulting in intrusion of water into the eyes. In case the goggles frame is made of a material having a hardness desirable for the rims 11, the hardness of the protective pads 12 and the bridge 111 will increase, thereby resulting in discomfort when wearing the swimming goggles. In addition, as the conventional goggles are made from a single molding material, the color obtained therein is the same throughout the goggles and is therefore insufficient to fulfill the consumers' demand for colorful products.

SUMMARY OF THE INVENTION

An object of the present invention is to provide a unitary goggles frame which has high stiffness in its lens rims to provide resistance against deformation, and good flexibility in its protective pads to provide a comfortable feeling and a good watertight seal between the goggles frame and the wearer's face.

Another object of the present invention is to provide a unitary goggles frame with different colors so as to present a good aesthetic appearance.

Still another object of the present invention is to provide a goggles frame which can be assembled with a pair of lenses without creating any clearance susceptible of leakage.

According to one aspect of the present invention, a goggles assembly has a one-piece molded frame which includes a pair of lens rims, a bridge interconnecting the lens rims, and a pair of looped protective pads connected to and lining the lens rims. The lens rims have a stiffness sufficient to resist deformation when subjected to a pulling force applied to the lens rims in opposite directions. The bridge has a stiffness different from that of the lens rims. The protective pads have flexibility and softness sufficient for flexing so as to conform to the profile of a wearer's face around the eyes thereof. The molded frame is fabricated from at least two different molding compositions, one of which has high stiffness to impart rigidity to the lens rims, and the other one of which imparts good flexibility to the protective pads.

According to another aspect of the present invention, a goggles assembly has a one-piece molded frame which includes a pair of lens rims, a bridge interconnecting the lens rims, and a pair of looped protective pads connected to and lining the lens rims. Each lens rim has an inner periphery confining a lens opening, an inner peripheral flange projecting into the lens opening from the inner periphery, and a lens abutment surface formed on the inner peripheral flange at one side opposite to the protective pads. The inner peripheral flange has a plurality of angularly spaced apart holes. A pair of lenses each have a cross-section substantially equal to that of the lens opening, a marginal portion disposed in abutment with the lens abutment surface, and a plurality of resilient barbed legs extending from the marginal portion into the holes.

BRIEF DESCRIPTION OF THE DRAWINGS

The exemplary preferred embodiment of the present invention will now be detailed with reference to the accompanying drawings, of which:

FIG. 4 is a sectional view of the mold of FIG. 3 in a closed state; and

FIG. 5 is a plan view of a goggles frame produced according to the present invention;

FIG. 6 is an elevation view of the goggles frame of FIG. 5; and

DETAILED DESCRIPTION OF THE PREFERRED EMBODIMENT

Figure 1:
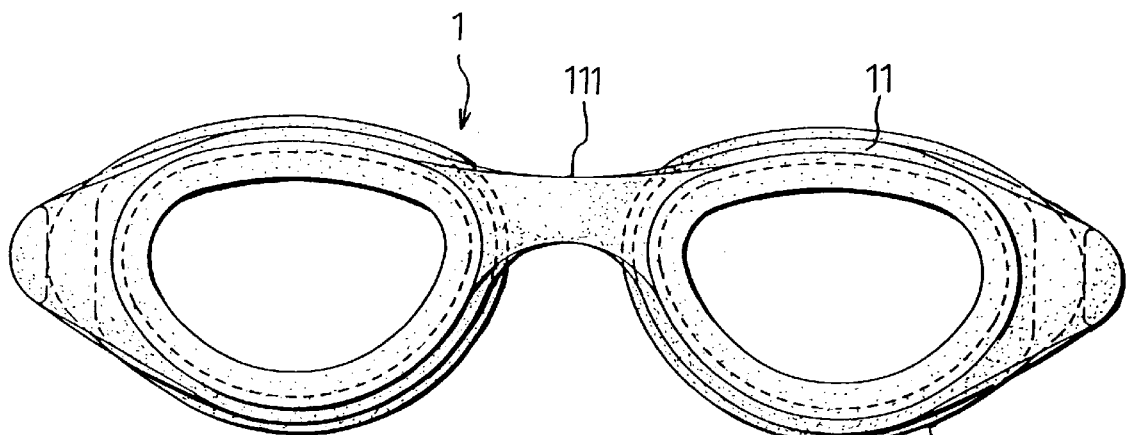
FIG. 1 is a plan view of a conventional pairs of goggles.
Figure 2:
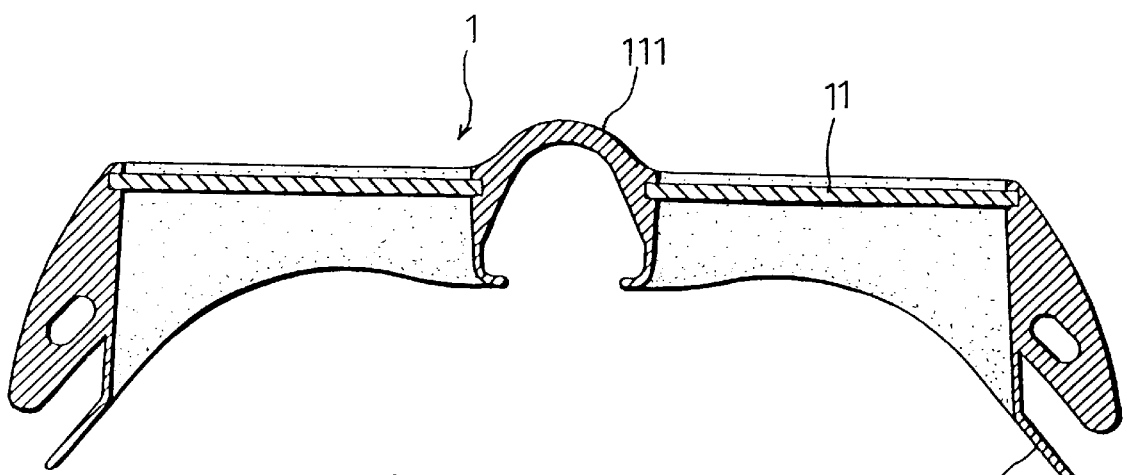
FIG. 2 is a sectional view of the conventional goggles.
Figure 3:
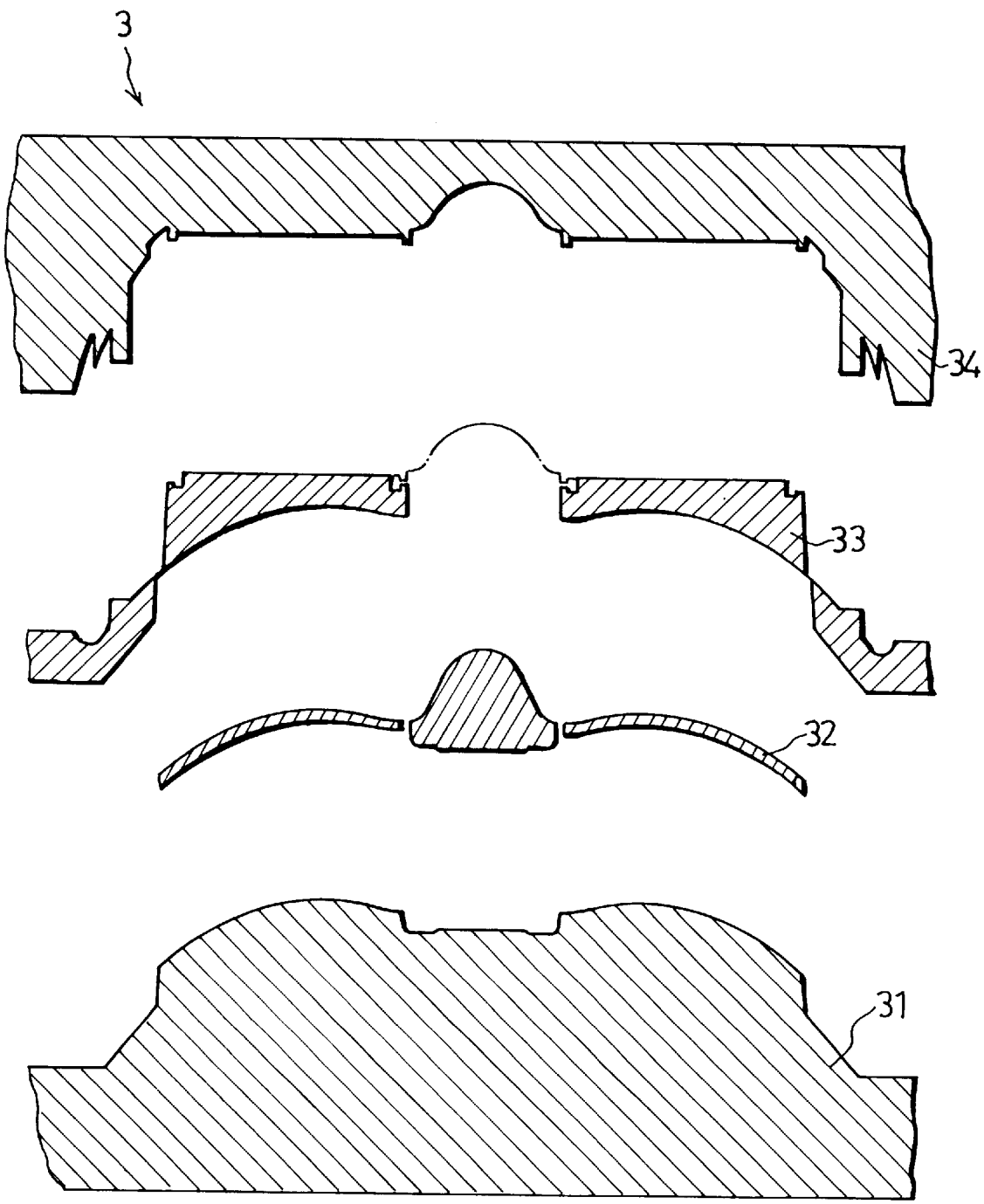
FIG. 3 is a sectional view of a mold for fabricating the goggles according to the present invention in an open state.

Referring to FIGS. 3, 4, 5 and 6, a goggles assembly embodying the present invention is shown to comprise a goggles frame 2 which is formed by compression molding via a mold 3 and which includes a pair of lens rims 21, a bridge 211 interconnecting the lens rims 21, and a pair of looped protective pads 213 connected to and lining the lens rims 21. The goggles frame 2 is then coupled with locking rings 4 and lenses 5 to form the goggles. A method for fabricating the goggles frame 2 is described as follows:

The first step in the method is to prepare the mold 3 which will impart a configuration conforming to the goggles frame 2. The mold 3 is constituted of a plurality of mold parts having different configurations, including a first mold part 31, a second mold part 32, a third mold part 33 and a fourth mold part 34.

The mold parts 31–34 are then loaded with different molding compositions which are preferably prepared from a thermoplastic rubber, silicone or polyvinylchloride. Specifically, a molding composition to form a pair of looped protective pads 213 is disposed on the first mold part 31. After the second and third mold parts 32, 33 are superimposed sequentially on the first mold part 31, amolding composition for forming the lens rims 21 and a molding composition for forming the bridge 211 are placed on the third mold part 33. Finally, the mold 3 is closed by disposing the fourth mold 34 on the third mold 33, thereby enclosing all of the molding compositions in the mold 3. Note that the molding compositions are particularly prepared to have different colors and different degrees of stiffness desired for the protective pads 213, the lens rims 21 and the bridge 211. The molding composition of the lens rims 21 has a high degree of stiffness, while the molding composition of the bridge 211 is less stiff than the lens rims 21, and the molding composition of the protective pads 213 is softer and more flexible than that of the bridge 211. After the molding compositions are placed in the mold 3, the mold 3 is heated so that the compositions melt and are combined together. After the mold 3 is cooled, an integrally molded unitary goggles frame 2 is formed.

As such, the lens rims 21 of the compression molded goggles frame 2 have a stiffness which is greater than that of the bridge 211 and which is sufficient to resist deformation that might occur when the wearer applies a pulling force to the goggles frame in opposition directions to wear the goggles. The protective pads 213 have a stiffness less than that of the bridge 211. In other words, the protective pads 213 are soft and flexible so that they can be flexed to conform to the profile of the wearer's face at the area around his/her eyes and to contact intimately therewith, thus providing a good seal against intrusion of water. In addition, since the colors of the molding compositions are arranged to be different, the protective pads 213, the bridge 211 and the lens rims 21 are different in color, thereby improving the aesthetic appearance of the goggles frame 2. Moreover, as the goggles frame 2 has good resistance against deformation when the user exerts a pulling force on the goggles frame 2 during wearing of the goggles, the service life of the goggles can be prolonged.

Figure 7:
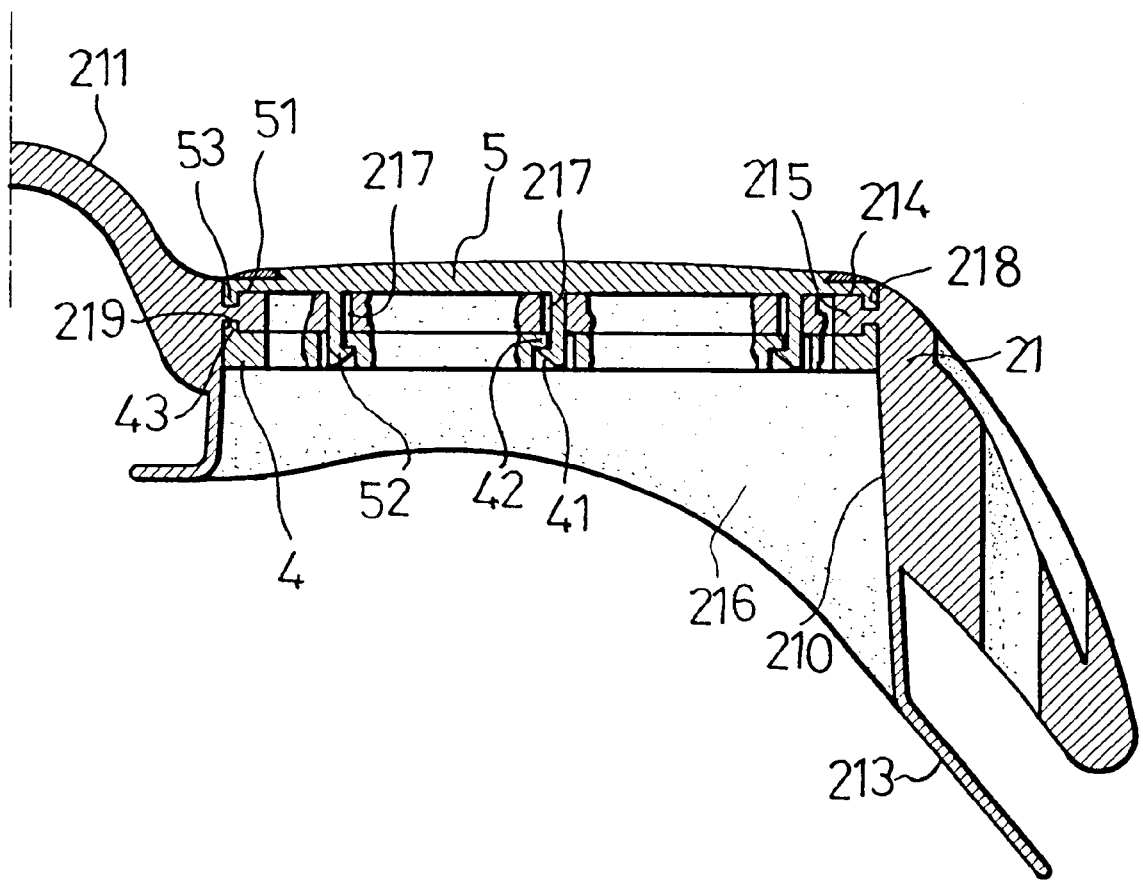
FIG. 7 is a fragmentary sectional view of the goggles frame of FIG. 5, with a lens and a locking ring attached thereto.

Referring again to FIG. 7, the goggles frame 2 as formed is a one-piece molded frame. Each lens rim 21 has an inner periphery 210 confining a lens opening 216, an inner peripheral flange 215 projecting from the inner periphery 210 into the lens opening 216, and a lens abutment surface 214 formed on the inner peripheral flange 215 opposite to the protective pads 213. The lens abutment surface 214 has a plurality of angularly spaced apart holes 217, and a first engagement groove 218 which extends around the holes 217 adjacent to the inner periphery 210.

Each lens 5 has a marginal portion 51 disposed in abutment with the lens abutment surface 214. The marginal portion 51 has an engagement end flange 53 which engages the first engagement groove 218 in the corresponding lens rim 21. A plurality of resilient barbed legs 52 extend from the lens 5 to the holes 217 in the lens rim 21, respectively.

A locking ring 4 is disposed in abutment with a corresponding lens rim 21 opposite to the corresponding lens 5. The locking ring 4 has a plurality of angularly spaced apart locking slots 41 aligned with the holes 217 of the lens rim 21, respectively. A protrusion 42 projects into a corresponding locking slot 41. The resilient barbed legs 52 of the lens 5 extend into the locking slots 41 via the holes 217, respectively, and engage the protrusions 42 of the locking ring 4, respectively, thereby retaining the barbed legs 52 in the respective locking slots 41. The locking ring 4 is further provided with an end flange 43 at its marginal portion so as to engage a second engagement groove 219 which is formed in the inner peripheral flange 215 at the side opposite to the first engagement groove 218. The second engagement groove 219 also extends adjacent to the inner periphery 210 of the lens rim 21 around the holes 217. The construction of the lenses 5 and the locking ring 4 as described above can prevent water from leaking through the lenses 5 and the lens rims 21.

While the present invention has been described in connection with what is considered the most practical and preferred embodiment, it is understood that this invention is not limited to the disclosed embodiment but is intended to cover various arrangements included within the spirit and scope of the broadest interpretation so as to encompass all such modifications and equivalent arrangements.

I claim:

1. A goggles assembly comprising a one-piece molded frame, said one-piece molded frame including a pair of lens rims, a bridge interconnecting said lens rims, and a pair of looped protective pads connected to and lining said lens rims, said lens rims having a stiffness sufficient to resist deformation when subjected to a pulling force applied to said lens rims in opposite directions, said protective pads having flexibility and softness sufficient for flexing so as to conform to the profile of a wearer's face around the eyes thereof, wherein said one-piece molded frame is fabricated from at least two different molding compositions, one of which has high stiffness to impart rigidity to said lens rims, and the other one of which imparts good flexibility to said protective pads.

2. The goggles assembly according to claim 1, wherein said molding compositions have different colors.

3. The goggles assembly according to claim 1, wherein said molded frame is fabricated from three different molding compositions having different colors.

4. The goggles assembly according to claim 1, further comprising a pair of lenses attached to said lens rims, respectively.

5. The goggle assembly of claim 1, wherein said rims, bridge, and pads are molded together into an integrally molded unitary frame.

6. A goggles assembly comprising a one-piece molded frame, said molded frame including a pair of lens rims, a bridge interconnecting said lens rims, and a pair of looped protective pads connected to and lining said lens rims, said lens rims having a stiffness sufficient to resist deformation when subjected to a pulling force applied to said lens rims in opposite directions, said bridge having a stiffness different from that of said lens rims, said protective pads having flexibility and softness sufficient for flexing so as to conform to the profile of a wearer's face around the eyes thereof, wherein said molded frame is fabricated from at least two different molding compositions, one of which has high stiffness to impart rigidity to said lens rims, and the other one of which imparts good flexibility to said protective pads;

wherein each of said lens rims has an inner periphery confining a lens opening, an inner peripheral flange projecting into said lens opening from said inner periphery, and a lens abutment surface formed on said inner peripheral flange at one side opposite to said protective pads, said inner peripheral flange having a plurality of angularly spaced apart holes; and a pair of lenses each having a cross-section substantially equal to that of said lens opening, a marginal portion disposed in abutment with said lens abutment surface, and a plurality of resilient barbed legs extending from said marginal portion into said holes.

7. The goggles assembly according to claim 6, wherein said abutment surface further includes a first engagement groove extending along said inner periphery and around said holes, each of said lenses further having an engagement end flange projecting from said marginal portion into said first engagement groove.

8. The goggles assembly according to claim 7, further comprising a locking ring disposed in abutment with a corresponding one of said lens rims opposite to the corresponding one of said lenses, said locking ring having a plurality of angularly spaced apart locking slots aligned with said holes respectively, and protrusions projecting into said locking slots, respectively, said resilient barbed legs extending into said locking slots via said holes, respectively, said protrusions engaging and retaining said barbed legs in said locking slots.

9. The goggles assembly according to claim 8, wherein each of said lens rims further has a second engagement groove extending in said inner peripheral flange opposite to said first engagement groove, said second engagement groove extending along said inner periphery and around said holes.

10. A goggles assembly comprising:
- a one-piece molded frame including a pair of lens rims, a bridge interconnecting said lens rims, and a pair of looped protective pads connected to and lining said lens rims, each of said lens rims having an inner periphery confining a lens opening, an inner peripheral flange projecting into said lens opening from said inner periphery, and a lens abutment surface formed on said inner peripheral flange at a side opposite to said protective pads, said inner peripheral flange having a plurality of angularly spaced apart holes; and
- a pair of lenses each having a cross-section substantially equal to that of said lens opening, a marginal portion disposed in abutment with said lens abutment surface, and a plurality of resilient barbed legs extending from said marginal portion into said holes.

11. The goggles assembly according to claim 10, wherein said abutment surface has a first engagement groove extending along said inner periphery and around said holes, each of said lenses further having an engagement end flange projecting from said marginal portion into said first engagement groove.

12. The goggles assembly according to claim 10, further comprising a locking ring disposed in abutment with a corresponding one of said lens rims opposite to the corresponding one of said lenses, said locking ring having a plurality of angularly spaced apart locking slots aligned with said holes respectively, and protrusions projecting into said locking slots, respectively, said resilient barbed legs extending into said locking slots via said holes, respectively, said protrusions engaging and retaining said barbed legs in said locking slots.

13. A goggles assembly comprising a one-piece molded frame, said one-piece molded framed including a pair of lens rims, a bridge interconnecting said lens rims, and a pair of looped protective pads connected to and lining said lens rims, said lens rims having a stiffness sufficient to resist deformation when subjected to a pulling force applied to said lens rims in opposite directions, said bridge having a stiffness smaller than that of said lens rims, said protective pads having flexibility and softness sufficient for flexing so as to conform to the profile of a wearer's face around the eyes thereof, wherein said one-piece molded frame is fabricated from three different molding compositions having different stiffnesses and forming said lens rims, said bridge and said protective pads, respectively.

14. The goggle assembly of claim 13, wherein said rims, bridge, and pads are molded together into an integrally molded unitary frame.

15. The goggle assembly of claim 13, wherein said three different molding compositions have at least two different colors.

* * * * *